(12) United States Patent
Hayashi (10) Patent No.: US 10,271,992 B2
(45) Date of Patent: Apr. 30, 2019

(54) PORTABLE DEVICE FOR TREATING MENIERE'S DISEASE AND SIMILAR CONDITIONS

(71) Applicant: DAIICHI MEDICAL CO., LTD., Tokyo (JP)

(72) Inventor: Masaaki Hayashi, Tokyo (JP)

(73) Assignee: DAIICHI MEDICAL CO., LTD., Tokyo (JP)

( * ) Notice: Subject to any disclaimer, the term of this patent is extended or adjusted under 35 U.S.C. 154(b) by 746 days.

(21) Appl. No.: 14/786,175

(22) PCT Filed: Apr. 22, 2014

(86) PCT No.: PCT/JP2014/061270
§ 371 (c)(1),
(2) Date: Nov. 24, 2015

(87) PCT Pub. No.: WO2014/175257
PCT Pub. Date: Oct. 30, 2014

(65) Prior Publication Data
US 2016/0067099 A1    Mar. 10, 2016

(30) Foreign Application Priority Data

Apr. 23, 2013  (JP) ................................ 2013-089949

(51) Int. Cl.
*A61F 11/00*    (2006.01)
*A61M 13/00*    (2006.01)
(Continued)

(52) U.S. Cl.
CPC .............. *A61F 11/00* (2013.01); *A61H 21/00* (2013.01); *A61H 23/04* (2013.01);
(Continued)

(58) Field of Classification Search
CPC .......... A61H 21/00; A61H 23/04; A61F 11/00
See application file for complete search history.

(56) References Cited

U.S. PATENT DOCUMENTS 2,264,442 A * 12/1941 James ...................... F23K 3/14
                                                110/308
4,754,748 A *  7/1988 Antowski ............... A61F 11/00
                                                600/559
(Continued)

FOREIGN PATENT DOCUMENTS

CN          1791370 A     6/2006
CN        101534883 A     9/2009
(Continued)

OTHER PUBLICATIONS

International Search Report for application PCT/JP2014/061270 dated Jul. 16, 2014.
(Continued)

*Primary Examiner* — LaToya M Louis
(74) *Attorney, Agent, or Firm* — Roberts Mlotkowski Safran Cole & Calderon, P.C.

(57) ABSTRACT

A portable device for noninvasively treating Meniere's disease and similar conditions by introducing pressure pulses into an ear canal to vibrate auditory ossicles through a tympanic membrane. The device includes a pump unit for generating the pressure pulses, wherein the pump unit includes a Voice Coil Motor and a diaphragm pump that is driven by the Voice Coil Motor; an earpiece for transmitting the pressure pulses to a tympanic membrane; a controller for controlling the pump unit; and an alarm lamp. When the device detects no pressure pulses being generated even when the pump unit is operated, the alarm lamp is lit and an error message is displayed on the indicator, and when the device detects the earpiece being disconnected from the ear of the (Continued)

user, the microcomputer stops counting the time elapsed and the alarm lamp is lit and an error message is displayed on the indicator.

2 Claims, 4 Drawing Sheets (51) Int. Cl.
*A61H 23/04* (2006.01)
*A61H 21/00* (2006.01)
*A61M 11/00* (2006.01)

(52) U.S. Cl.
CPC ... *A61M 13/003* (2013.01); *A61H 2201/1207* (2013.01); *A61H 2201/5071* (2013.01); *A61H 2205/027* (2013.01); *A61M 11/005* (2013.01); *A61M 2205/07* (2013.01); *A61M 2205/3365* (2013.01); *A61M 2210/0662* (2013.01)

(56) References Cited

U.S. PATENT DOCUMENTS

| | | | |
|---|---|---|---|
| 4,757,807 A | | 7/1988 | Densert et al. |
| 4,984,579 A | | 1/1991 | Burgert et al. |
| 5,868,682 A | * | 2/1999 | Combs ............... A61B 5/121 600/559 |
| 6,629,938 B1 | | 10/2003 | Engvall et al. |
| 2003/0181851 A1 | | 9/2003 | Mann et al. |
| 2004/0225178 A1 | * | 11/2004 | Kriewall ............... A61F 11/04 600/25 |
| 2006/0030837 A1 | * | 2/2006 | McKenna ............... A61F 11/00 604/890.1 |
| 2007/0060948 A1 | | 3/2007 | Franz et al. |
| 2008/0082059 A1 | | 4/2008 | Fink et al. |
| 2008/0103447 A1 | | 5/2008 | Reggiardo et al. |

FOREIGN PATENT DOCUMENTS

| | | |
|---|---|---|
| EP | 0266474 A1 | 5/1988 |
| JP | S63127753 A | 5/1988 |
| JP | 2002153499 A | 5/2002 |
| JP | 2002519150 A | 7/2002 |
| JP | 2002523149 A | 7/2002 |
| JP | 2008080137 A | 4/2008 |
| JP | 4308438 B2 | 8/2009 |
| JP | 2010508123 A | 3/2010 |
| WO | 9308775 A1 | 5/1993 |
| WO | 9723178 A1 | 7/1997 |
| WO | 0001331 A2 | 1/2000 |
| WO | 03099176 A1 | 12/2003 |

OTHER PUBLICATIONS

Chinese Office Action for corresponding Chinese Patent Application dated Jul. 12, 2016.
Extended European Search Report for corresponding European Patent Application No. 14787439.0 dated Oct. 12, 2016.
Office Action issued in the corresponding Chinese Application No. 201480023145.1 dated Sep. 27, 2017.
Decision to Grant issued in the corresponding JP application No. 2014-561210 dated Aug. 25, 2015 (Machine Translation).
Development of medical devices for evasively alleviating dizziness attacks of refractory Ménière's disease Heisei 24 year problem-solving medical equipment development project research results report (summary version) [online], Oct. 2013, p. 1-30, [Search Jun. 16, 2015].
Y. Watanabe et al., Intermittent pressure therapy of intractable Meniere's disease and delayed endolymphatic hydrops using the transtympanic Membrane massage device: a preliminary report, Acta Oto-Laryngologica, 2011, vol. 131, No. 11, p. 1178-1186 (English Abstract).
Office Action issued in the corresponding TW application No. 103114501 dated Oct. 25, 2017.
"Development of medical devices for evasively alleviating dizziness attacks of refractory Ménière's disease" Heisei 24 year problem-solving medical equipment development project research results report (summary version) [online], Oct. 2013, p. 1-30, [Search Jun. 16, 2015]—Machine translation provided.

* cited by examiner

PORTABLE DEVICE FOR TREATING MENIERE'S DISEASE AND SIMILAR CONDITIONS

TECHNICAL FIELD

The present invention relates to a portable device for treating Meniere's disease and similar conditions by introducing pressure pulses into the ear canal to vibrate the auditory ossicles through the tympanic membrane.

BACKGROUND ART

Meniere's disease is known as a disease of the inner ear that is associated with repeated symptoms of vertigo, hearing loss, tinnitus, and occlusive feeing in ear. It develops from endolympathic hydrops. A method to prevent or repress the development of Meniere's disease is known to improve the metabolism of ear fluid by vibrating the auditory ossicles through the tympanic membrane. Herein, preventing or repressing the development of Meniere's disease is called the treatment of Meniere's disease.

Conventionally, a device for massaging the tympanic membrane by vibrations of air, which is also called a massaging device for the tympanic membrane, has been known. The massaging device for the tympanic membrane is used for stimulating the tympanic membrane so as to treat otosclerosis or secretory otitis media. It just has to massage so that the patient feels good. Thus the pressure and period of the massage can be generally adjusted by the patient.

However, in a massage for treating Meniere's disease a precise pressure waveform, such as the pressure, the frequency, and widths of the pulses, and their period, that are suitable to treat the disease, must be correctly transmitted to the inner ear. Thus a conventional massaging device for the tympanic membrane lacks some functions.

The massage for treating Meniere's disease should be done multiple times a day. However, to go to a treatment facility for every massage burdens the patient. Thus a device for the treatment that can be transported by the patient and operated by the patient has been anticipated. Though such a device has been developed, it is far from being practical in use.

For example, a device that is disclosed by Japanese Patent No. 4308438 introduces vibrations in air pressure generated by a pressure generating unit to the patient's external ear via a flexible tube. The vibrations in the external ear are introduced to the inner ear through a tiny tube that is implanted in the tympanic membrane to provide the vibrations in the air pressure of the inner ear. Since the device uses the tube implanted in the tympanic membrane to provide the vibrations in the air pressure of the inner ear, it is invasive. In such a case a need to surgically implant the tube burdens the patient. Further, a possible ingress of water through the tube has a disadvantage in ordinary life. Further, a follow-up is required for about one month after implanting the tube. Thus the start of care is delayed. Further, the tube must be removed after complete recovery. Further, a risk exists that the aperture in the tympanic membrane may not be closed up.

A device for relieving symptoms of Meniere's disease by applying a positive or negative pressure to the ear canal is disclosed in U.S. Pat. No. 4,984,579. By that device, once the patient switches it on, the pressure in the external ear is gradually increased or reduced to one that is predetermined by a medical doctor, etc., via a probe that is inserted in the external ear. After a predetermined period, the pressure is returned to the atmospheric pressure. That is, the device is to apply a static pressure on the external ear for a predetermined period. Thus little effects by massage can be achieved. Further, as safety equipment the device has only a switch to quickly return the pressure to the atmospheric pressure. So, there is no way to check if the right treatment has been given. The device is not sufficient to be used by a patient to treat Meniere's disease.

The purpose of the present invention is to provide a portable and small and light device for treating Meniere's disease and similar conditions that gives a safe and correct treatment when it is used by the patient.

DISCLOSURE OF INVENTION

Figure 1:
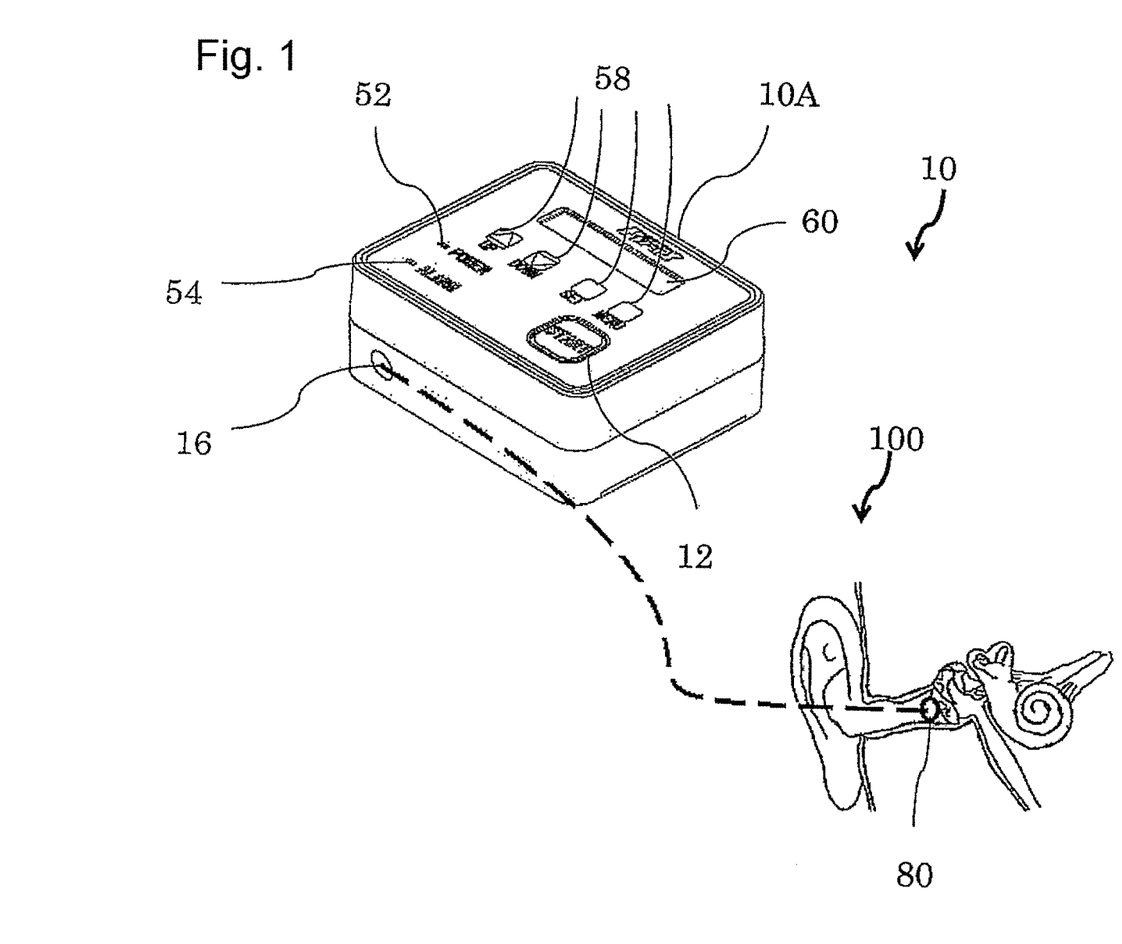
FIG. 1 is a schematic diagram of the device for the treatment of the present invention.
Figure 3:
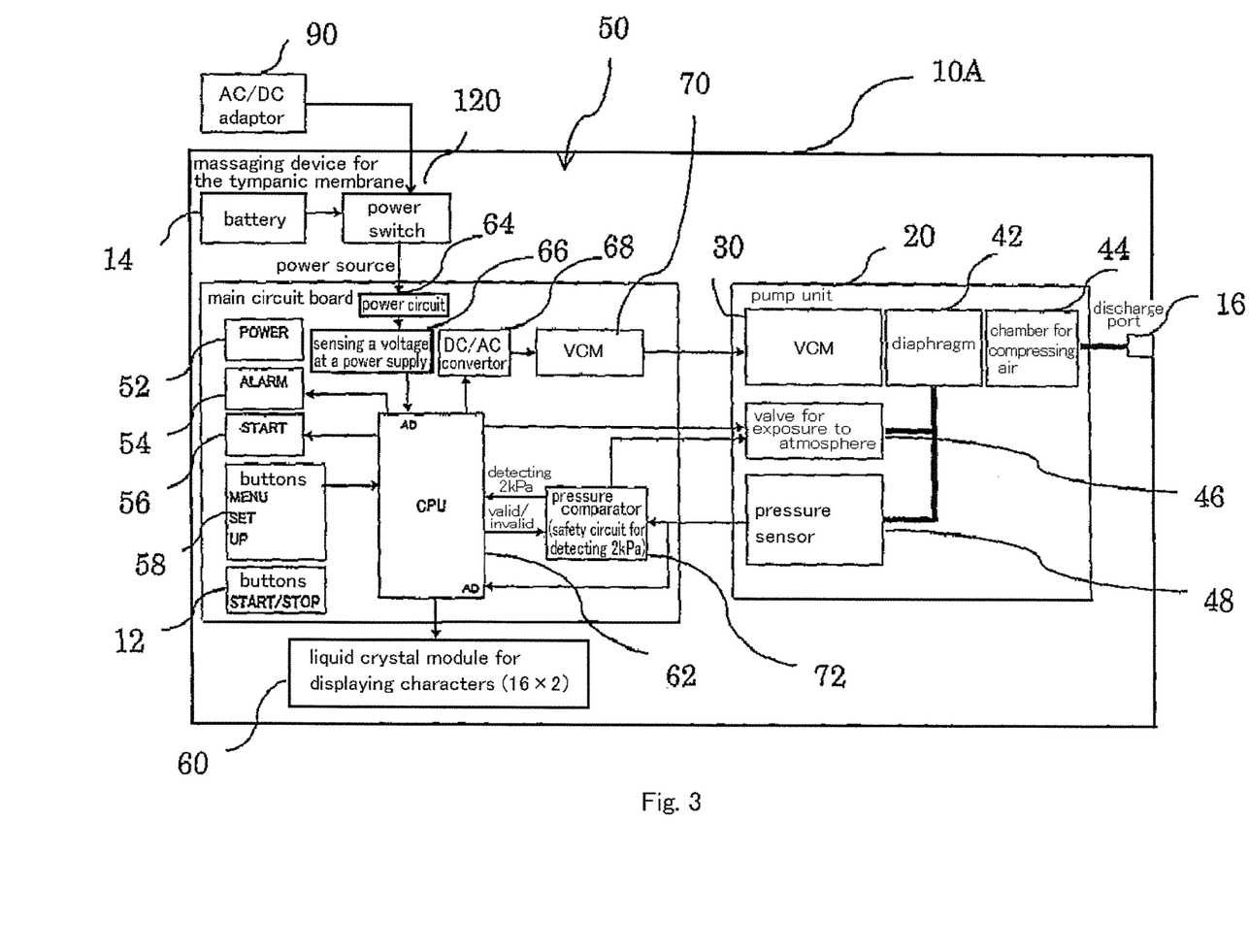
FIG. 3 is a block diagram of the system of the device for the treatment of the present invention.

To solve the above problems, as in FIGS. 1 and 3 for example, the device of the first aspect of the present invention is a portable device 10 for treating Meniere's disease and similar conditions by introducing pressure pulses into the ear canal to vibrate the auditory ossicles through the tympanic membrane. It comprises a pump unit 20 for generating the pressure pulses, an earpiece 80 for transmitting the pressure pulses to the tympanic membrane, and a controller 50 for controlling the pump unit 20. In that device the period, the pressure, the width, and the frequency of the pulses are adjustable.

By that configuration, since the period, the pressure, the width, and the frequency of the pulses that are introduced to the ear canal can be adjusted, the device can perform a massage that is best for the patient and achieve an excellent treatment of Meniere's disease and similar conditions.

In the device of the second aspect of the present invention, which uses the device of the first aspect, the operation mode of the device is selected from two modes, a first mode, in which a user can change any of the period, the pressure, the width, and the frequency of the pressure pulses, and a second mode, in which a user cannot change any of them.

By that configuration, the device can be used for treating Meniere's disease and similar conditions, where the period, the pressure, the width, and the frequency of the pressure pulses that have been set by a medical doctor, etc., are always used, and as a massaging device for the tympanic membrane to cause the patient to feel good.

Figure 2:
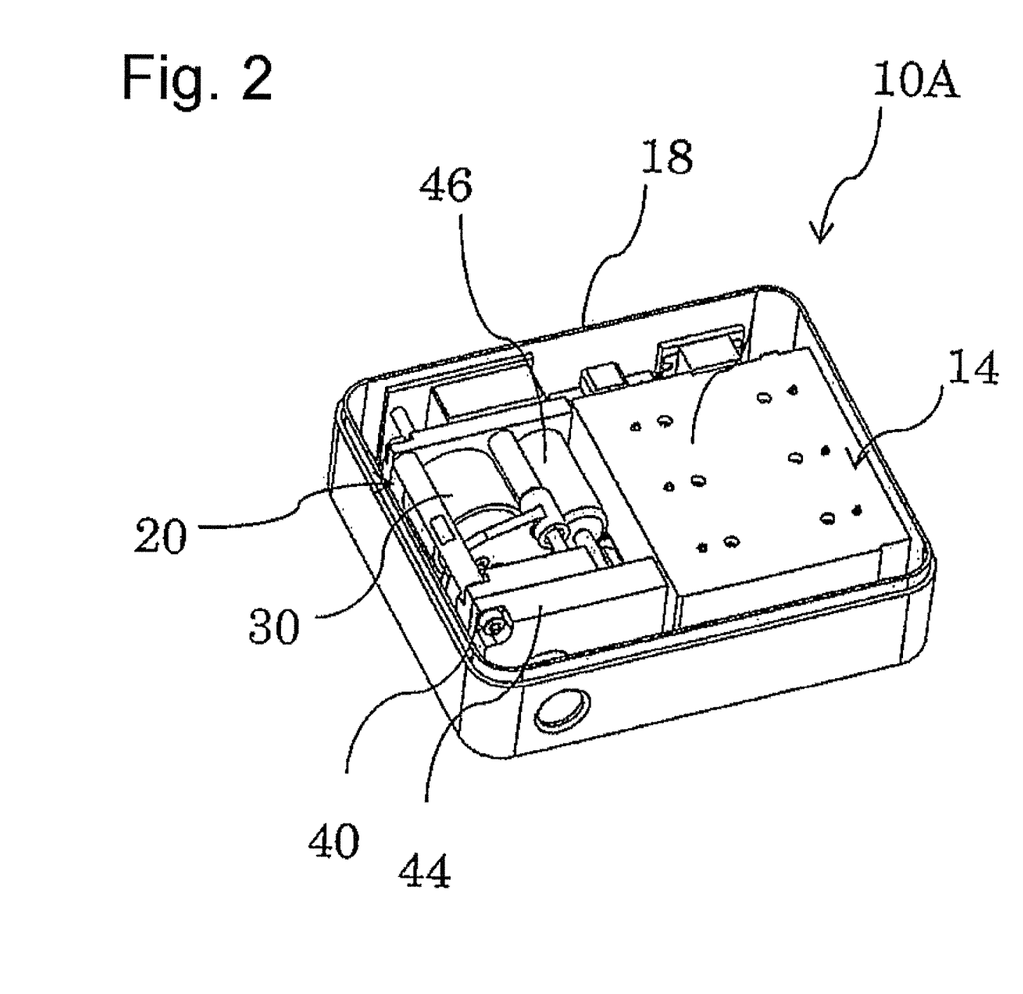
FIG. 2 is a perspective view of the inside of the main part of the device for the treatment of the present invention.

As in FIGS. 2 and 3, for example, the device of the third aspect of the present invention, which uses the device of the first or second aspect, further comprises a pressure sensor 48 for sensing a pressure of the pressure pulses, a circuit 66 for sensing a voltage on a power-supply, and a valve 46 for exposing compressed air in the chamber 44 for compressing air where the pressure pulses are generated to an atmospheric pressure. The device has the functions of detecting the earpiece 80 being disconnected from the ear 100 of the user, detecting when pressure pulses exceed the preset pressure, detecting no pressure reset in the chamber 44 for compressing air to the atmospheric pressure even when the valve 46 is opened to the atmospheric pressure, detecting no earpiece 80 being connected to the pump unit 20, detecting no pressure pulses being generated even when the pump unit 20 is operated, and detecting a voltage sensed by the circuit 66 being below a rated voltage.

By that configuration, no user can operate the device when the earpiece is disconnected from the ear. Further, since no pressure pulses exceed the preset pressure, the device is safe. Further, since the pressure in the chamber for compressing air is checked to see if it becomes the atmospheric pressure by opening the valve, pressure pulses that have the correct pressure are transmitted to the tympanic membrane. Further, no user operates the device when the earpiece is disconnected from the pump unit. Further, any malfunction in the pump unit can be detected. Further, any depression in the voltage on the power-supply can be detected. Thus the device provides a safe and reliable treatment.

As in FIG. 2 for example, in the device of the fourth aspect of the present invention, which uses the device of any of the first, second, and third aspects, the pump unit 20 comprises a Voice Coil Motor 30 and a diaphragm pump 40 that is driven by it.

By that configuration, since the pressure pulses are generated by the diaphragm pump that is driven by the Voice Coil Motor, the device is light and small and generates accurate pressure pulses.

By the light and small device for treating Meniere's disease and similar conditions of the present invention, which can be transported by the patient, since the period, the pressure, the width, and the frequency of the pressure pulses can be adjusted, it is suitable for the treatment of Meniere's disease and similar conditions and provides a safe and reliable treatment when it is used by the patient.

The basic Japanese Patent Application, No. 2013-089949, filed Apr. 23, 2013, is hereby incorporated by reference in its entirety in the present application.

The present invention will become more fully understood from the detailed description given below. However, the detailed description and the specific embodiments are only illustrations of the desired embodiments of the present invention, and so are given only for an explanation. Various possible changes and modifications will be apparent to those of ordinary skill in the art on the basis of the detailed description.

The applicant has no intention to dedicate to the public any disclosed embodiment. Among the disclosed changes and modifications, those which may not literally fall within the scope of the present claims constitute, therefore, a part of the present invention in the sense of the doctrine of equivalents.

The use of the articles "a," "an," and "the" and similar referents in the specification and claims are to be construed to cover both the singular and the plural, unless otherwise indicated herein or clearly contradicted by the context. The use of any and all examples, or exemplary language (e.g., "such as") provided herein is intended merely to better illuminate the invention, and so does not limit the scope of the invention, unless otherwise stated.

BEST MODE FOR CARRYING OUT THE INVENTION

Below, the embodiments of the present invention are discussed with reference to the drawings. The same numeral or symbol is used for the elements that correspond to, or are similar to, each other. Thus duplicated descriptions are omitted.

FIG. 1 is a schematic diagram of an embodiment of a device 10 for treating Meniere's disease and similar conditions (below, also called "the device for the treatment"), which device is small and light and so can be transported by a patient. The device 10 for the treatment comprises a main part 10A of the device for the treatment that generates desired pressure pulses and an earpiece 80.

FIG. 2 is a perspective view of the inside of the main part 10A of the device for the treatment. As in FIG. 2, the main part 10A has a pump unit 20 and a battery case 14. The pump unit 20 has a Voice Coil Motor 30 and a diaphragm pump 40. Though a controller 50 is placed inside the main part 10A, it is not shown. It is a control board that is, for example, placed to cover the upper plane in FIG. 2.

The Voice Coil Motor 30 is used for driving the diaphragm pump 40 so that it is directly driven by electric energy. That is, if a rotary motor with a stator and a rotor were to be used, a rotating motion of an output shaft would have to be converted to a linear motion via a cam mechanism, etc. However, if the Voice Coil Motor 30 is used, no cam is used, so that the main part 10A becomes small and light. The Voice Coil Motor 30 has a faster response than that of a solenoid, which also generates a linear motion directly from electric energy. Thus it accurately drives the pump. Incidentally, the diaphragm pump 40 may be driven by any other means, such as a rotary motor, a solenoid, etc.

The diaphragm pump 40 has a diaphragm 42 (see FIG. 3) that is driven by the Voice Coil Motor 30 and a chamber 44 for compressing air of which the volume is changed by the movement of the diaphragm 42. Since the structure of the diaphragm pump is commonly known, the detailed description of it is omitted. Incidentally, a machine for generating pressure pulses is not limited to a diaphragm pump, but may be any other known machine. By the diaphragm 42, the structure can be simplified so that the main part 10A can become small and light.

A power source for the device 10 for the treatment may be AC household electric power that is to be converted by an AC/DC power supply adapter 90. Alternatively, it may be a commercial battery or batteries. A commercial battery may be lighter than a battery charger.

These components 14, 20 and the controller 50, which is discussed below, are put in a case 18 that is, for example, made of plastic. In the figure the case 18 is shown as a generally rectangular parallelepiped that can be easily placed on a table. If the main part 10A is very small, it may be worn like an ear-hook type or a headphone or it may be suspended from a neck by a string, etc.

The earpiece 80 transmits the pressure pulses that have been generated in the main part 10A of the device for the treatment to the tympanic membrane. It is made of an elastic material, such as a silicone rubber. It has a passage through which the pressure pulses are transmitted to the tympanic membrane. The pressure pulses are caused by the changes in volume in the chamber 44 for compressing air. The changes are generated by the movement of the diaphragm 42. The shape of the earpiece 80 may be an oval, but any shape that may suit the shape of the external ear of the patient can be used.

Since the earpiece 80 that is attached to the main part 10A of the device for the treatment is inserted into the external ear for stimulating the tympanic membrane, the treatment is noninvasive. Thus the burden on the patient is low and the safety is high. Further, the treatment can be quickly started. By vibrating the tympanic membrane and the auditory ossicles by the air pressure by means of the earpiece 80 for the treatment of Meniere's disease, the metabolism of inner ear fluid can be noninvasively improved. By vibrating the tympanic membrane and the auditory ossicles by the air pressure by means of the earpiece 80 for the treatment of otosclerosis or secretory otitis media, an air flow is generated in the middle ear.

Now the pressure pulses that are generated by the main part 10A of the device for treatment are discussed. The period, the pressure, the width, and the frequency of the pressure pulses (below, collectively called "the operation modes") are adjustable. Herein the term "pressure" means the maximum value of the positive pressure or negative pressure of the pressure pulses. The term "width" of the pulses means a period when a positive or negative pressure of the pressure pulses occurs. The shape of the pressure waveform is important for an effective treatment of Meniere's disease. Thus the width of pulses must be adjusted. If both the positive pressure pulses and the negative pressure pulses must be used for stimulating the tympanic membrane, the respective widths of the positive and negative pressure pulses are separately set. The term "frequency" means a frequency of a cyclic pressure waveform. The frequency determines how often the pulse is transmitted when the pressure and the width of pulses are constant.

Next, with reference to FIG. 3, the operation of the device 10 for the treatment is discussed. FIG. 3 is a block diagram of the system of the device for the treatment of the present invention.

The controller 50 controls the pump unit 20 to generate the pressure pulses. It also monitors the device 10 for the treatment so as to provide a safe and reliable treatment. Thus, as discussed below, it has some sensors 48, 66, a microcomputer 62 for processing data, some displays 52, 54, 60, and some operating devices 12, 58.

Once the power switch 120 is turned on, electric power is supplied to the main part 10A of the device for the treatment to light a power light (an LED for indicating power) 52. The pressure pulses are not yet generated. The voltage that has been input to the controller 50 is converted to a rated voltage by a power circuit 64. A circuit 66 for monitoring the power checks to see if the voltage becomes below the rated one (7.2 V, for example). That is, the battery 14 is checked to see if a sufficient voltage is maintained while the pressure pulses are generated. If the voltage were to be below the rated one, the pump unit 20 would possibly not generate the correct pressure pulses. Thus an alarm lamp (an LED for displaying an alarm) 54 is lit and a warning of a weak battery is displayed on an indicator (a liquid crystal module for displaying characters) 60. The operation of the pump unit 20 is immediately stopped. The valve 46 for exposing compressed air to the atmospheric pressure is opened so that no subsequent operation can be done. Thus a failure caused by a low voltage can be avoided.

The device 10 for the treatment provides a mode (the first mode) in which the patient can set the operation modes of the pressure pulses by oneself. By this mode, the patient sets the period and the pressure that are comfortable for him or her. The operation modes that were set are stored even when the power is turned off. When the power is next turned on the operation modes are set as they were. The setting of the operation modes is changed if necessary. In this way, the device 10 for the treatment can be used not only for the treatment of Meniere's disease, etc., but also for the treatment of otosclerosis, etc., like a conventional massaging device for the tympanic membrane. By the first mode, only the period and the pressure of the pressure pulses can be set like a conventional massaging device and the width of pulses and the frequency may be predetermined.

In the device 10 for the treatment the operation modes for the treatment of Meniere's disease, etc., are input by a medical doctor or an administrator who acts under the instructions of a medical doctor (collectively called "the doctor, etc.") to be tailored to the patient. The hardness of the tympanic membrane, the length of the ear canal, and the relationship with the auditory ossicles, differ from one patient to another. The operation modes that are the most suitable for the treatment of Meniere's disease, etc., i.e., the period, the pressure, the width, and the frequency of the pressure pulses, differ from one patient to another. Thus a medical doctor selects the precise operation modes for the treatment at a clinical site. The operation modes are input by the doctor, etc., before the treatment. Thus the device 10 provides a mode (the second mode) in which only an allowed person, i.e., the doctor, etc., can set the operation modes, for example, by inputting an administrator's code. The second mode may be set or deactivated or the operation modes can be input only when the administrator's code is input. Once the operation modes are input, the patient cannot change them. For the treatment of Meniere's disease, etc., the second mode should be selected in the device 10 for the treatment. Thus the treatment can always be done under the best operation modes.

The mode is set or the operation modes are input by pressing buttons for manual operation 58 in accordance with the contents displayed on the indicator 60. The indicator 60 displays "Setting Mode," "Timer x min. x sec.," "Pressure x kPa," "Width of Pulse x ms.," "Frequency x Hz," etc. Incidentally, the mark "x" indicates a number. The buttons for manual operation 58 include, for example, an UP button for upwardly shifting the list of the functions or numbers, a DOWN button for downwardly shifting them, a SET button for approving a number or function that is shown on the screen, and a MENU button for changing the menu that is displayed. The buttons for manual operation 58 may include a numeric keypad for inputting a number and a knob for changing a number.

After the setting of the operation modes is completed (if the second mode is selected, no setting is required for any activation), a start (START/STOP) button is pressed so as to start the treatment. When the start button is pressed, the setups of the operation modes may be sequentially displayed for confirmation.

After confirming the setups of the operation modes, as in FIG. 1 the earpiece 80 is inserted in an ear to be treated. If an ear-hook type (not shown) is used for the device for the treatment, the main part 10A is hooked on the auricle and the earpiece 80 is inserted in the ear. If the main part 10A of the device for the treatment is to be suspended by a string or to be placed on a table, a connecting tube 82, 84 (see FIG. 4) is connected to the main part 10A. The earpiece 80 that is attached to the end of the connecting tube 82, 84 is inserted in the ear.

When the earpiece 80 is inserted in the ear, the pressure in the chamber 44 for compressing air of the pump unit 20 slightly increases because the earpiece 80 is sealed. The pressure in the chamber 44 for compressing air is measured by a pressure sensor that is located in the pump unit 20. Then a valve for exposing compressed air to the atmospheric pressure (an electromagnetic valve) 46 is opened so that the pressure in the chamber 44 that has increased is decreased for some seconds. Immediately after the pressure returns to the atmospheric pressure the valve 46 is closed.

If no pressure returns to the atmospheric pressure, the valve 46 may be out of order. Unless the operation is started after the pressure returns to the atmospheric pressure, no reliable treatment at the set pressure can be done. Thus an alarm lamp 54 is lit and an error message is displayed on the indicator 60. No subsequent operation can be done.

When the pressure returns to the atmospheric pressure a voltage that has been converted to an alternating current (AC) voltage by a DC/AC converter of the controller 50 is applied from a VCM drive 70 to the pump unit 20, i.e., the Voice Coil Motor (VCM) 30. By applying the AC voltage to the Voice Coil Motor 30 the driving shaft linearly reciprocates to drive the diaphragm 42. That is, the diaphragm pump 40 generates the pressure pulses. At this time the indicator 60 has a display showing if the device 10 is operated at a so-called mode of a massaging device for the tympanic membrane (the first mode) or at a mode for the treatment of Meniere's disease, etc. (the second mode). It also displays the time elapsed from the start of the operation and the remaining time.

When the operation is started, the pressure sensor 48 keeps on detecting the pressure. If no pressure changes after the pump unit 20 operates, the pump unit 20 or the pressure sensor 48 may be out of order. Thus the alarm lamp (an LED for displaying an alarm) 54 is lit and an error message is displayed on the indicator 60. The operation is stopped.

If the preset pressure (for example, the pressure that is higher than the set pressure by 0.5 kPa, or the pressure that is higher than 4 kPa) is detected, the operation is quickly stopped. At the same time that the operation is stopped, the alarm lamp 54 is lit and an error message is displayed on the indicator 60. In this case, a failure of the controller 50 or a malfunction of the pump unit 20 or the pressure sensor 48 is possible. In this way, any excessive pressure is prevented from acting on the tympanic membrane, so that the safety is improved.

If the earpiece 80 is disconnected from the ear 100, the pressure cannot increase to the set pressure. In this case, the microcomputer 62 stops counting the time elapsed. The alarm lamp 54 is lit and an error message is displayed on the indicator 60. When the earpiece 80 is again inserted into the ear and the start button 12 is pressed, the operation is restarted so that the time elapsed is counted. By again inserting the earpiece 80 into the ear, the pressure in the chamber 44 for compressing air slightly increases. Like the process at the start of the operation, the change in the pressure is detected by the pressure sensor 48 so as to open the valve 46 for exposing compressed air to the atmospheric pressure to return the pressure to the atmospheric pressure. Then the pressure pulses are generated. That is, even if the earpiece 80 is disconnected from the ear in mid-course, the treatment can be done at the set operation modes. Thus a reliable treatment can be given when the device 10 for the treatment is operated by the patient.

If the earpiece 80 is disconnected from the main part 10A of the device for the treatment, i.e., from a connector 16 of the chamber 44 for compressing air, the pressure cannot increase to the set pressure and highly negative pressure may be detected. In this case, the microcomputer 62 also stops counting the time elapsed. The alarm lamp 54 is lit and an error message is displayed on the indicator 60. The operation of the pump unit 20 is stopped. The valve 46 is opened so that the pressure returns to the atmospheric pressure. If the vibrations of the pressure are stopped after the operation is restarted, then the earpiece 80 is determined to be damaged. The alarm lamp 54 is lit and an error message is displayed on the indicator 60. The operation is stopped.

Figure 4:
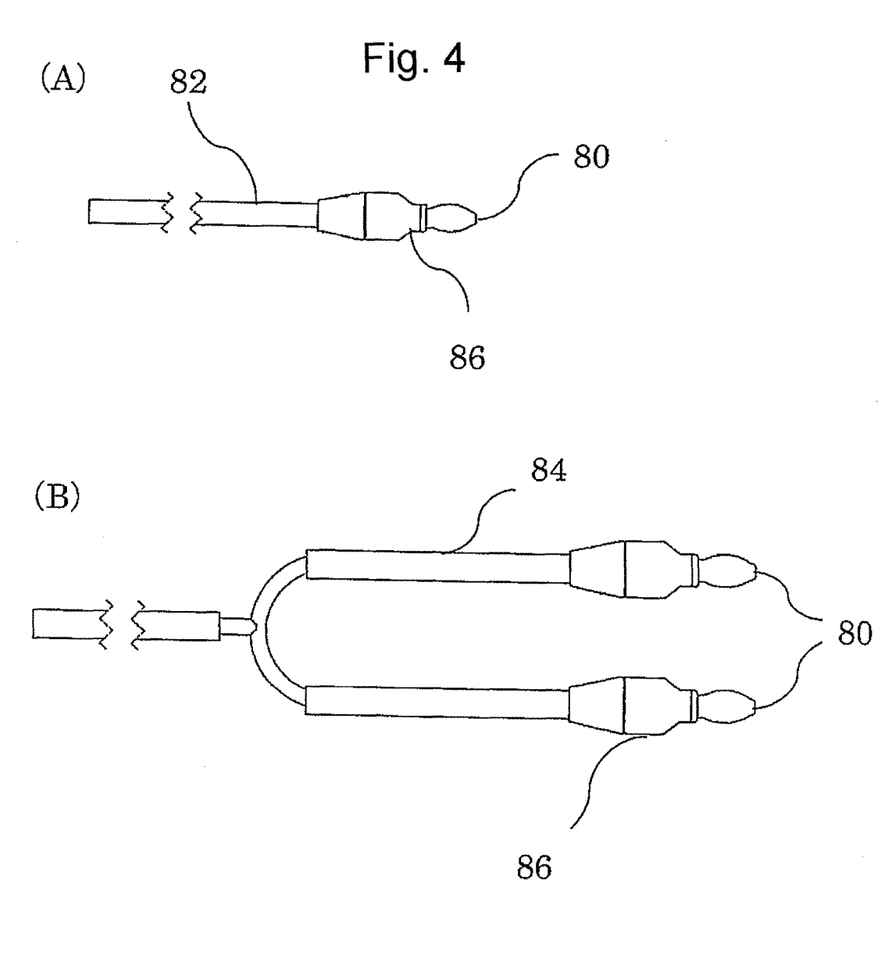
FIG. 4 is a schematic diagram illustrating some examples of the connecting tubes.

When the connecting tube 82, 84 is used between the main part 10A of the device for the treatment and the earpiece 80, the same abnormal change is detected for the connecting tube 82, 84 that is damaged. If the vibrations of the pressure are stopped after the operation is restarted, then the connecting tube 82, 84 is determined to be damaged. The alarm lamp 54 is lit and an error message is displayed on the indicator 60. The operation is stopped.

When a predetermined time has passed while a failure is watched during an operation as discussed above, the operation automatically ends. Thus the treatment by applying the pressure set by the accurate operation modes to the tympanic membrane can certainly be given.

FIG. 4 is a schematic diagram illustrating the examples of the connecting tube 82, 84 that connects the main part 10A of the device for the treatment with the earpiece 80. FIG. 4(A) illustrates an example of the connecting tube 82 for the main part 10A of the device for the treatment that is used for Meniere's disease, etc., (the second mode) and that is suspended by a string or placed on a table. Since a single ear is generally massaged in the treatment of Meniere's disease, etc., the connecting tube 82 is connected to one piece of the earpiece 80. The connecting tube 82 is a tube that is made of a flexible material such as rubber. However, its thickness is such that its diameter hardly changes. Thus the pressure pulses generated by the movement of the diaphragm 42 can remain unchanged. FIG. 4(B) illustrates an example of the connecting tube 84 for the device 10 for the treatment that is used as a massaging device for the tympanic membrane (the first mode). Since the massaging device for the tympanic membrane massages both ears at one time, the end to be connected to the connection 16 is a single one. But the connecting tube 84 branches to two so that two pieces of the earpiece 80 can be attached.

Between the connection 16 of the main part 10A of the device for the treatment or the connecting tube 82, 84 and the earpiece 80 a connection for the ear pad 86 that facilitates connecting them and prevents earwax from entering the connecting tube 82, 84 may be provided. The connection for the ear pad 86 may have a strainer that prevents earwax from entering.

Though the pressure sensor 48 is discussed as being located in the chamber 44 for compressing air of the diaphragm pump 40, it may be alternatively or additionally provided in the earpiece 80 or the connection for the ear pad 86. When the respective pressure sensors 48 are provided to both the chamber 44 for compressing the air and the earpiece 80 or the connection for the ear pad 86, disconnection of the earpiece 80 or damage in the connecting tube 82, 84 is certainly detected.

Below, the main reference numerals and symbols that are used in the detailed description and drawings are listed.
10: a device for the treatment
10A: the main part of the device for the treatment
12: the start button
14: the battery case
18: the case
20: the pump unit
30: the Voice Coil Motor
40: the diaphragm pump
42: the diaphragm
44: the chamber for compressing air
46: the valve for exposing compressed air to the atmospheric pressure (an electromagnetic valve)
48: the pressure sensor
50: the controller
52: the power light (an LED for indicating power)
60: an indicator (a liquid crystal module for displaying characters)
66: the circuit for sensing the voltage on a power-supply 80: an earpiece
82: a connecting tube
84: a connecting tube
86: the connection for an ear pad
90: the AC/DC adaptor
100: an ear
120: the power switch

The invention claimed is:

1. A portable device for noninvasively treating Meniere's disease and similar conditions by introducing pressure pulses into an ear canal to vibrate auditory ossicles through a tympanic membrane, the device comprising:
   a pump unit for generating the pressure pulses, wherein the pump unit comprises a Voice Coil Motor and a diaphragm pump that is driven by the Voice Coil Motor;
   an earpiece for transmitting the pressure pulses to a tympanic membrane;
   a controller for controlling the pump unit;
   a pressure sensor for sensing a pressure of the pressure pulses;
   a circuit for sensing a voltage on a power-supply;
   a valve for exposing compressed air in a chamber for compressing air where the pressure pulses are generated to an atmospheric pressure;
   an alarm lamp;
   an indicator; and
   a microcomputer that counts time elapsed from start of operation,
   wherein a period, a pressure, a width, and a frequency of the pressure pulses are adjustable, wherein respective widths of a positive and a negative pressure pulse are separately set,
   wherein pressure pulses that are suitable for the treatment of Meniere's disease are generated,
   wherein the device has the functions of detecting the earpiece being disconnected from the ear of a user, detecting when pressure pulses exceed a preset pressure, detecting no pressure reset in the chamber for compressing air to the atmospheric pressure when the valve is opened to the atmospheric pressure, detecting no earpiece being connected to the pump unit, detecting no pressure pulses being generated when the pump unit is operated, and detecting a voltage sensed by the circuit being below a rated voltage,
   wherein when the device detects no pressure pulses being generated when the pump unit is operated, the alarm lamp is lit and an error message is displayed on the indicator, and
   wherein when the device detects the earpiece being disconnected from the ear of the user, the microcomputer stops counting the time elapsed and the alarm lamp is lit and an error message is displayed on the indicator.

2. The device of claim 1, wherein an operation mode of the device is selected from two modes: a first mode, in which a user can change any of the period, the pressure, the width, and the frequency of the pressure pulses, and a second mode, in which the user cannot change any of them.

* * * * *